US010390750B2

(12) United States Patent
Jensen et al.

(10) Patent No.: US 10,390,750 B2
(45) Date of Patent: *Aug. 27, 2019

(54) DEVICE FOR MEASURING PRESSURE IN A FLUID

(71) Applicant: Andromeda Medizinische Systeme GmbH, Munich (DE)

(72) Inventors: Michael Gondy Jensen, Jyderup (DK); Kristine Larsen, Munich (DE); David Van Gorkom, Prien am Chiemsee (DE); Jens Witte, Munich (DE)

(73) Assignee: ANDROMEDA MEDIZINISCHE SYSTEMS GmbH, Taufkirchen/potzham (DE)

( * ) Notice: Subject to any disclaimer, the term of this patent is extended or adjusted under 35 U.S.C. 154(b) by 844 days.

This patent is subject to a terminal disclaimer.

(21) Appl. No.: 14/772,351

(22) PCT Filed: Feb. 28, 2014

(86) PCT No.: PCT/EP2014/053967
§ 371 (c)(1),
(2) Date: Sep. 2, 2015

(87) PCT Pub. No.: WO2014/135456
PCT Pub. Date: Sep. 12, 2014

(65) Prior Publication Data
US 2016/0029941 A1 Feb. 4, 2016

(30) Foreign Application Priority Data
Mar. 4, 2013 (DE) .................. 10 2013 102 085

(51) Int. Cl.
*A61B 5/20* (2006.01)
*G01L 9/00* (2006.01)
(Continued)

(52) U.S. Cl.
CPC ............ *A61B 5/205* (2013.01); *A61B 5/4255* (2013.01); *G01L 9/0001* (2013.01);
(Continued)

(58) Field of Classification Search
CPC ...................................................... A61B 5/205
See application file for complete search history.

(56) References Cited

U.S. PATENT DOCUMENTS 4,621,647 A 11/1986 Loveland
5,827,243 A 10/1998 Palestrant
(Continued)

FOREIGN PATENT DOCUMENTS

DE 02026127 B2 12/1971

*Primary Examiner* — Daniel L Cerioni
*Assistant Examiner* — Yasmeen S Warsi
(74) *Attorney, Agent, or Firm* — Douglas Denninger

(57) ABSTRACT

A measurement chamber, and a device for measuring pressure in a fluid, the device including a coupling element, at least one pressure transducer and at least one measuring chamber that can be filled with a fluid. The measurement chamber is mechanically coupled to the measurement surface of the pressure transducer by a membrane. The measurement chamber has at least two connection points for a fluid flow. The at least one pressure transducer is arranged in the coupling element, and the at least one measurement chamber has two outer webs opposite each other, one of the webs engaging a clamping edge of the coupling element and the other web engaging a pressing roller. The pressing roller is rotatably supported and can be connected to the coupling unit in a force-closed manner.

14 Claims, 5 Drawing Sheets

(51) Int. Cl.
　　　*G01L 19/00*　　　　(2006.01)
　　　*A61B 5/00*　　　　(2006.01)
(52) U.S. Cl.
　　　CPC ........ *G01L 19/003* (2013.01); *G01L 19/0023* (2013.01); *A61B 2560/0443* (2013.01); *A61B 2562/0247* (2013.01); *A61B 2562/043* (2013.01)

(56) References Cited

U.S. PATENT DOCUMENTS

| | | | |
|---|---|---|---|
| 6,056,697 | A | 5/2000 | Owens et al. |
| 6,725,726 | B1 | 4/2004 | Adolfs et al. |
| 2003/0200812 | A1 | 10/2003 | Kuhn et al. |
| 2004/0006321 | A1* | 1/2004 | Cheng ................. A61F 5/44 604/349 |
| 2004/0050168 | A1* | 3/2004 | Uberreiter ........... A61M 1/3639 73/706 |
| 2005/0065408 | A1 | 3/2005 | Benderev |
| 2007/0038143 | A1 | 2/2007 | Christensen et al. |
| 2008/0250340 | A1 | 10/2008 | Dlugos et al. |
| 2009/0131768 | A1* | 5/2009 | Simpson ............. A61B 5/0031 600/309 |
| 2009/0221933 | A1 | 9/2009 | Nishtala et al. |
| 2009/0288494 | A1* | 11/2009 | Henes ................ G01L 19/0023 73/744 |
| 2014/0100526 | A1 | 4/2014 | Ueda et al. |

* cited by examiner

DEVICE FOR MEASURING PRESSURE IN A FLUID

CROSS-REFERENCE TO RELATED APPLICATIONS

This application is a national phase filing under 35 USC § 371 of international application No. PCT/EP2014/053967 filed 28 Feb. 2014, which claims priority to German Application No. 10 2013 102 085.2 filed 4 Mar. 2013. This application also cross-references the following two international applications by the same inventors and having the same filing dates in the US, WIPO and Germany: PCT/EP2014/053968 for "Pressure-Measuring System" and PCT/EP2014/053970 for "Device For Regulating A Volumetric Flow Rate". The entire contents of each of the above-mentioned applications are incorporated herein by reference.

FIELD OF THE INVENTION

The present invention relates to a device for measuring pressure in a fluid, more particularly for medical diagnosis and a measurement chamber for use in the device for measuring pressure in a fluid, more particularly in the field for urodynamics and gastroenterology.

BACKGROUND OF THE INVENTION

In the prior art diagnostic pressure measurement, particularly in urodynamics is known. Inter alia, in pressure measurement with water-filled catheters, the pressure in the body is directed via a water column which passes through the lumen of the catheter and the pressure transmission housed, to external pressure sensors. There the pressure in the body is measured, including a hydrostatic pressure which is determined from the difference in height between the measurement indicator and the measurement location. This pressure offset is compensated either through a defined positioning of the sensor (at pubic bone height in urodynamics) or through electronic zeroing.

Nowadays a urodynamic examination requires a considerable amount of preparation and a large number of sterile disposable articles are needed. A pump tube, a perfusion tube, three pressure measurement indicators each with a three- and a two-way valve, three pressure transmission tubes, a transurethral catheter with a filling and two measuring volumes and rectal catheter with a balloon which have to be set up and prepared at the site of measurement (FIG. 1).

Disadvantageous, however, is the very complicated, error-prone and time-consuming handling involved. Each of the various individual steps has to be carried out in the presence of, in most cases, restless to nervous patients, which even in the case of experienced users often leads to errors and a large number of disposable articles is needed, which frequently leads to logistical problems.

SUMMARY OF THE INVENTION

On the basis of this prior art, it is now the aim of the present invention to provide a device for measuring pressure in a fluid with which the known drawbacks of the prior art are at least partially overcome or improved.

This aim achieved through a device in accordance with the invention for measuring pressure in a fluid according to claim 1, Preferred forms of embodiment of the device for measuring pressure in a fluid and of the measurement chamber are the subject matter of the relevant sub-claims. The invention also covers the use of the measurement chamber in the field of urodynamics and gastroenterology, more particular for bladder, rectal and urethral pressure measurement.

The present invention relates to a device for measuring pressure in a fluid, comprising a holder, also referred to herein as a coupling element, at least one pressure transducer and at least one cassette having at least one measurement chamber which can be filled with a fluid, wherein the measurement chamber is mechanically coupled to the measurement surface of the pressure transducer by means of a membrane. The device is characterised in that the at least one pressure transducer is arranged in the coupling element and the cassette has two outer flanges, also referred to herein as webs positioned opposite each other, wherein one of the webs engages in a clamping edge of a first clamping portion of the coupling element and the other web engages in a pressing roller, wherein the pressing roller is held in a rotatable manner at a second clamping portion of the holder.

Considered as fluids in accordance with the present invention are flowable systems, more particularly liquids, which are, for example, used in medicine and medical technology. Examples of these can be infusion solutions such as sodium chloride solution, water, aqueous solutions, solutions for injection, solutions for infusion, nutritional solutions, electrolyte solutions, blood, plasma, gas, air, combinations thereof and suchlike.

In accordance with a further particularly preferred form of embodiment these fluids are stored in fluid reservoirs which, in turn, are also known in the prior art, in the form of infusion bottles or infusion bags for example.

In accordance with a preferred form of embodiment the pressure transducer is an electro-mechanical pressure transducer and preferably at least the measurement area of the pressure transducer is covered in a force-fitting manner by the membrane. Alternatively, or in combination, the measurement area of the pressure transducer is arranged centrically in relation to the surface area of the measurement chamber.

The measurement chamber also preferably has an essentially circular base area, wherein alternatively or in combination the area is open and/or the membrane covers the open area and/or the membrane is made of a material selected from a group containing silicone, latex, rubber, combinations thereof and suchlike. In addition, in accordance with a further particularly preferred form of embodiment, the membrane is an integral part of the measurement chamber. In another preferred form of embodiment the measurement chamber is essentially dome-shaped and/or the dome-shaped interior centrally has a flattened area. This is also designed in such a way that it can take up a volume of fluid of between 0.1 cm$^3$ and 10 cm$^3$, preferably between 1 cm$^3$ and 5 cm$^3$ and/or the surface area of the measurement chamber is between 0.1 cm$^2$ and 5 cm$^2$, preferably between 1 cm$^2$ and 2.5 cm$^2$.

In accordance with a further, particularly preferred form of embodiment, the device in accordance with the invention for measuring pressure in a fluid comprises at last two, preferably a plurality, of measurement chambers, which are preferably directly or indirectly connected to each other at a web-free outer edge.

According to the present invention, the measurement chamber and/or the coupling element are at least in sections, or partially, made of a material that is selected from a group that includes duroplastic or thermoplastic synthetic materials, and more particularly polyphenylene sulphide, polypropylene, poly-1-butene, polyvinyl chloride, polyvinylidene chloride, polymethyl methacrylate, polyacryl nitrile, polystyrene, polyacetal, polyvinyl alcohol, polyvinyl acetate, ionomers, fluoroplastic, polyethylene, polyamide, more particularly partially aromatic polyamide, polycarbonate, polyester, polyphenylene oxide, polysulphone, polyvinyl acetal, polyurethane and chlorinated polyether, cellulose nitrate, cellulose acetate, cellulose ether, phenol resin, urea resin, thiourea resin, melamine resin, alkyl resin, allyl resin, silicone, polyimide, polybenzimidazole, epoxy resin, casein plastic, cross-linked polyurethane, unsaturated polyester resin, acrylnitrile butadiene styrene, acrylester styrene acrylonitrile, metals such a stainless steel, aluminium, combinations thereof and suchlike.

The connection points for the fluid flow, which is fed into the measurement chamber and out of the measurement chamber are, in a particularly preferred form of embodiment of the present invention, arranged at an angle ($\alpha$) with regard to each other of 180° to 60°, preferably at an angle of 180° to 120°, particularly preferably at an angle of 144° to 115°, more particularly at an angle of approx. 150°. In addition, and alternatively, the connection points are arranged at an angle ($\beta$) of 0° to 60°, preferably of 12° to 18°, preferably of less than 60° and more particularly of approximately 15° with regard to the base area of the measurement chamber.

In a further form of embodiment, in order to be able to connect the connection points as simply as possible to a tubing system, the connection points individually, or in combination, have a positive or negative Luer lock connection.

In order to connect the measurement chamber to the pressure transducer, the pressure transducer is arranged in a coupling element and the measurement chamber(s) is/are connected via the outer webs of the measurement chamber (s) and the clamping edge of the coupling element in such a way that via the flexible membrane the internal pressure in the measurement chamber can be determined via the pressure transducer. So that the connection between the coupling element and the measurement chamber can take place as simply as possible, the coupling element has a pressing roller into which a web of the measurement chamber engages and which is then stopped via a rotary movement of the pressing roller and at the same time provides the necessary pressing force for connecting the measurement chamber to the pressure transducer. Through this rotation, the measurement chamber, the membrane and the pressure transducer are preferably connected to each other in a fluid-tight manner or for the transmission of the internal pressure of the measurement chamber. The pressing roller can be rotated manually or also via a motor, more particularly an electric motor, a multiphase motor or a servo motor.

The aim of the invention is also achieved, in addition to the device for measuring pressure, by a measurement chamber that can be filled with a fluid for use in a device for measuring pressure with at least two connection points for a fluid flow. The connection points for the input and output of the fluid are arranged at an angle ($\alpha$) of 180° to 60°, preferably at an angle of 180° to 120°, particularly preferably at an angle of 144° to 115°, more particularly at an angle of approximately 150° with regard to each other. Alternatively, or in combination, the connection points can also be arranged at an angle ($\beta$) of 0° to 60°, preferably of 12° to 18°, preferably of less than 60° and more particularly of approximately 15° to the base area of the measurement chamber. As has already been set out with regard to the device, in accordance with a further, preferred form of embodiment at least one of the connection points is provided with a positive or negative Luer lock connection.

The base area is taken to mean the area which is aligned to the pressure transducer of the device for pressure measurement during the measurement. The connection points are also, and in accordance with a particularly preferred form of embodiment, arranged at a distance from the base area of 2 to 10 mm, preferably 4 to 8 mm and particularly preferably 6 mm and alternatively or in combination at least one of the opening of the connection points in the interior of the measurement chamber has a moulding at least in sections which faces the base area.

The interior of the measurement chamber preferably also has an essentially circular base area, wherein this is open and/or the membrane covers the open base area. In accordance with a further particularly preferred form of embodiment of the invention the membrane is made of a material which is selected from a group which contains silicone, latex, rubber, combinations thereof and suchlike. The interior of the measurement chamber can also essentially be dome-shaped and/or flattened in the central area. Also, on at least two opposite outer edges the measurement chamber also comprises webs, wherein alternatively or in combination at least one further measurement chamber is arranged on at least one of the web-free edges.

The present invention also expressly covers the use of the previously described measurement chamber for a device for measuring the pressure of fluid(s), wherein the measurement chamber and device are used, among other things and preferably in medicine and medical technology, more particularly in the field of urodynamics and gastroenterology, more particularly for bladder, rectal and urethral pressure measurement.

The invention will be described below with the aid of a preferred example of embodiment, whereby it is pointed out that the invention is not restricted to the embodiment illustrated here, but also to appropriate deviations in the sense of the invention.

DETAILED DESCRIPTION OF THE PRESENTLY PREFERRED EMBODIMENTS

Figure 1:
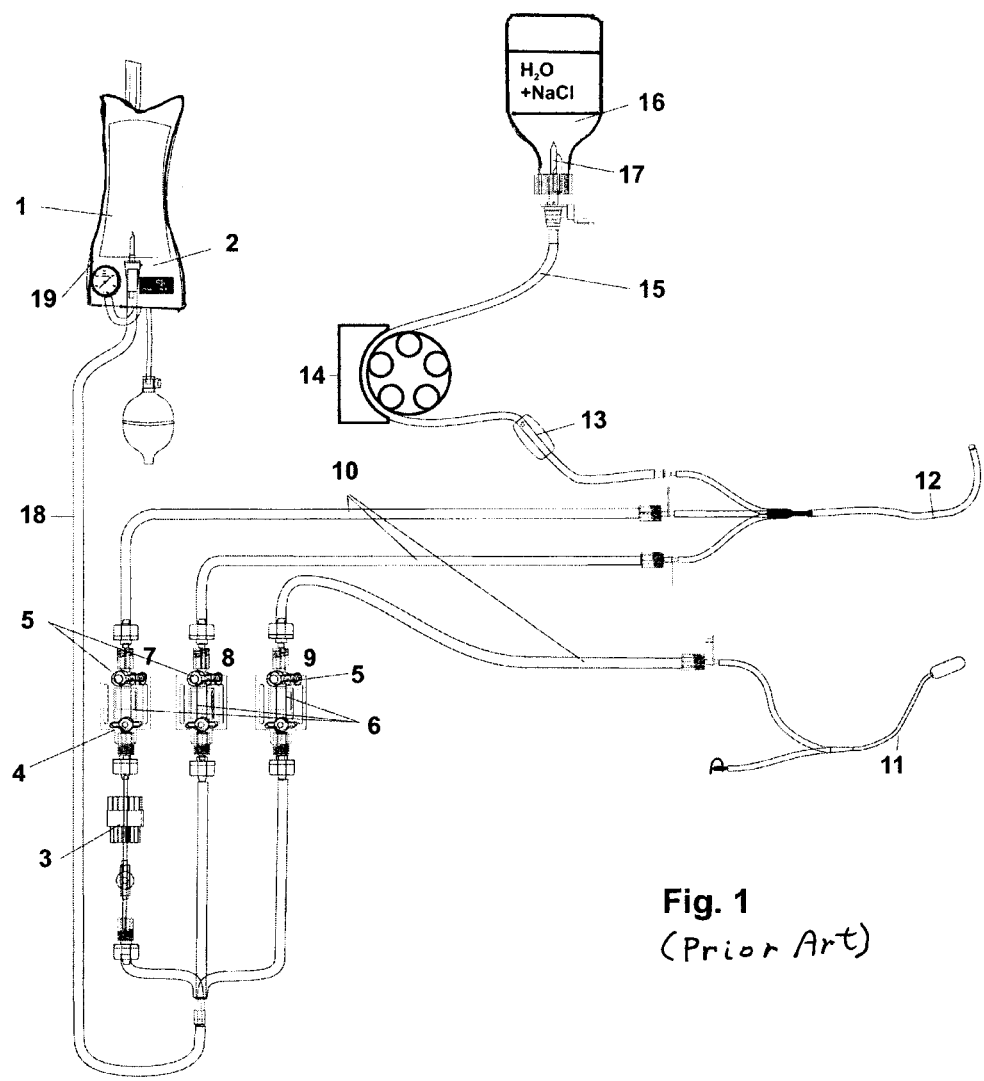
FIG. 1 shows the structure of a measuring system in accordance with the prior art.

FIG. 1 schematically shows the structure of a device for measuring pressure with water-filled disposable catheters. In addition to the bag with a solution for infusion 1 and a pressure cuff 2, a pressure transducer 3 and two-way valves 4 before the pressure sensors 6 are shown. Connected to these are three-way valves 5 and the corresponding tubes are designated as $P_{ura}$ 7, $P_{ves}$ and $P_{abd}$ 9. Via the pressure transmission hoses 10 the solution for infusion is supplied from the bag 1 to the rectal catheter 11 and the urethral pressure profile (UPP) catheter 12. In addition from the bottle 16 with, for example, a saline solution, via the roller pump 14 and the drip chamber 13, the saline solution is supplied to the UPP catheter 12 from the bottle 16.

The preparation and measuring procedure is carried out as follows:

a) The pump tube 15 is inserted into the pump 14 and the spike connection 12 of the hose inserted into the bottle stopper. The pump 14 is switched on until the drip chamber 13 of the bottle 16 is half filled and the tube is filled with saline solution completely free of bubbles.

b) The three pressure measurement indicators 6 are placed in the holders and connected to the perfusion tube 18—between the perfusion tube and one pressure measurement indicator a flow transducer 3 is inserted. The spike connection 19 of the perfusion hose 18 is inserted into the water bags 1.

c) The pressure transmission hoses 10 are connected to the pressure measurement indicators 6.

d) All two-way 4 and three-way valves 5 are closed and the pressure cuff 2 is pumped up to pressurise the water bags 1.

e) To vent the pressure transmission tubes the two-way 4 and three-way valves 5 of the pressure transducer are set to "open" and are filled, without bubbles, to the top with water and the two-way valve 2 is closed again. This procedure must be carried out individually for all three pressure transmission lines.

f) The three-way valves 5 are now individually turned into the 90° position in order to electronically adjust the pressure channel to atmospheric pressure by pressing a button. The three-way valves 5 are then turned to the "open" position again.

g) The two catheters 11, 12 are placed in the urethra and rectum of the patient and connected to the pressure transmission lines and the pump hose 10.

h) The three-way valves 5 must now be individually opened again individually in order to vent the two lumens of the transurethral catheter 12 up to the tip and to fill the balloon of the rectal catheter 11.

i) The measured pressures are checked and, if necessary, zeroed by software. The system is now ready for measurement.

Figure 2:
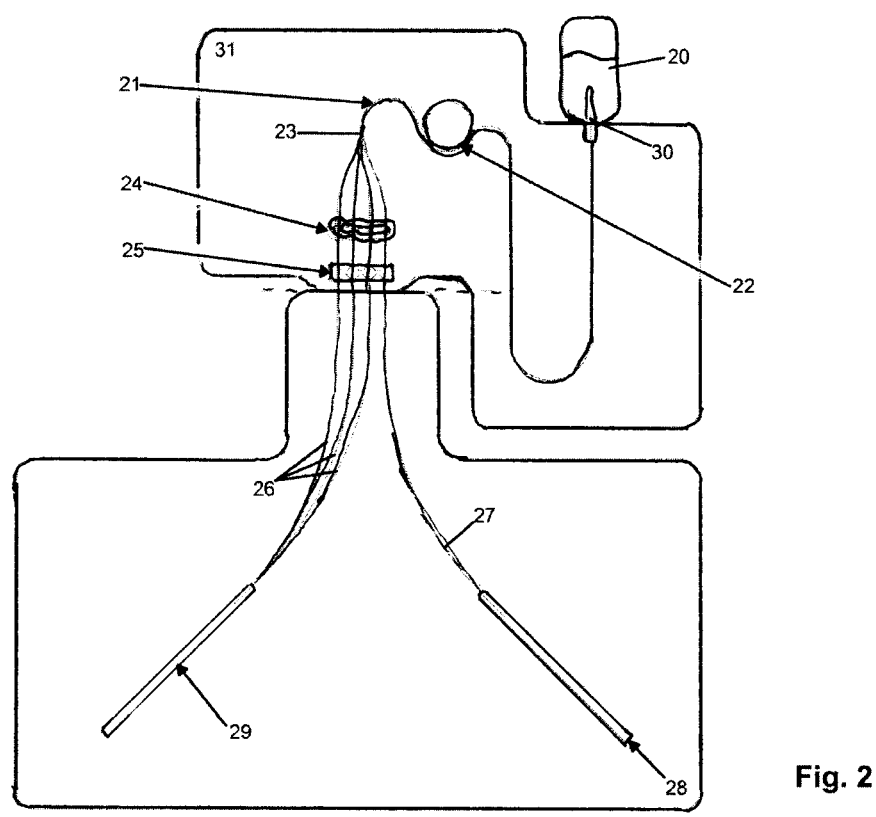
FIG. 2 shows the structure of a pressure measuring system in accordance with the present invention.

In FIG. 2 the set-up of a pressure measuring system in accordance with the invention is shown.

With reference number 21 this figure shows the pump tube leading to the pressure dome cassette 25 with the Luer locks for the connection of catheters 28 and 29. The spike connector 30 for standard infusion bottles 20 is also shown. 29 denotes the transurethral and 28 the rectal catheter (possible also any number of catheters or measuring volumes) which are supplied with the fluid via the lines 26 (three stages) and 27. Arranged adjoining this is the locking mechanism of the dome cassette 25. Arranged in the area denoted as 24 are four (possibly any number) of tube clips with the statuses "open", "closed" and "perfused". A roller pump 22 for conveying the medium through the hose system is shown. The system also has a control system 31 with a fully automated algorithm for venting the tube system with catheters, determining rest pressure and zeroing the measuring system using the functionality of the individual components.

Figure 3:
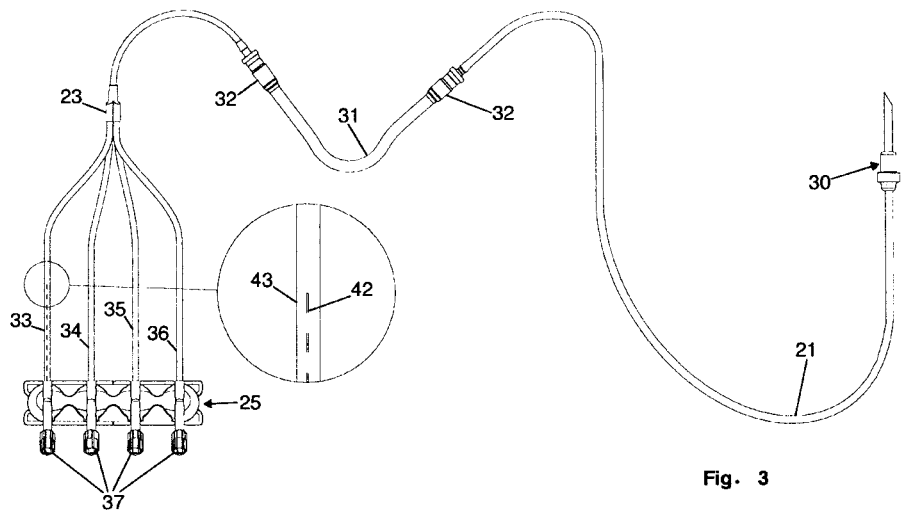
FIG. 3 shows a detailed view of a pump hose for the pressure measuring system in accordance with the invention.

Integrated into the pump tube—as shown in FIG. 3—are the infusion tubing 21, the venting tubing 34 to 36 three—possibly any number of—pressure channels and the dome cassette 25. The pump/infusion tubing 21 also has a spike connector 30 for an infusion bag and the Luer locks 37 for connecting the catheter. When this system is used with a roller pump the tubing system in this area has a suitable compressible tubing section 31 which through corresponding connectors 32 can be integrated into the tubing system. Via the distributor 23 the tubing system is divided into the four tubes 33 to 36 shown here. In addition to the actual tube 42, tube 33 has a spacer 43 as shown in the detailed view in FIG. 3.

Particularly advantageous in the present invention is the integration of three—possibly any number—of domes in a dome cassette and the common coupling of the channels to the sensors via a pressing roller and the clamping edge. Webs integrated into the dome cassette act on the pressing roller and clamping edge side as spring elements, which produce the required pressing pressure of the membranes, which are preferably arranged on the base section of the pressure domes, on the sensors.

This design has the great advantage over the conventional solution with individual domes that production is very much more cost-effective and handling is extremely simplified. Instead of placing each dome individually on its sensor as in the previous solutions, it is sufficient to insert the cassette which through the subsequent pressing of a button is turned with the pressing roller into the "closed" position via an actuator. The previously high number of required sterile components is reduced to a single disposable product.

As in many areas of application the sensor can be placed above the measuring locations in the body, as a result of the hydrostatic force of the water column negative pressures (lower than atmospheric pressure) also occur in the dome which are then not measured through pressure on the sensor surface but through tension. To produce the suction effect required for this the contacting between the membranes and sensor must be completely airtight. For this a pressing force is required.

Figure 4:
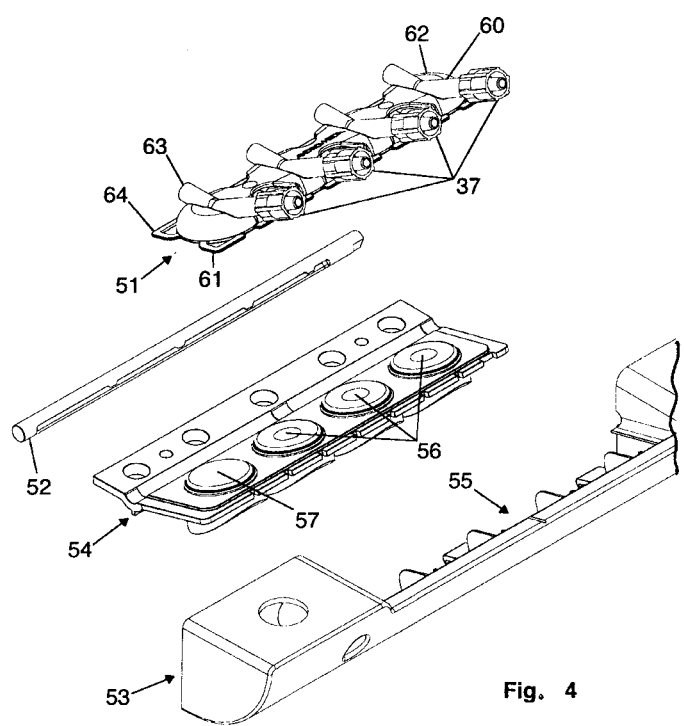
FIG. 4 shows an exploded view of the assembly of the pressure dome cassette with the pressure measuring sensors.

FIG. 4 shows an exploded view of the assembly of the pressure dome cassette 51 with the pressure measurement sensors 54. In addition to the dome cassette 51, the pressing roller 52, the holder 53 with the clamping edge 55 can be seen. Reference number 56 denotes the positions in relation to the dome cassette 51 which are fitted with a pressure measurement indicator. In position 57 no pressure measurement indicator is envisaged.

Figure 5C:
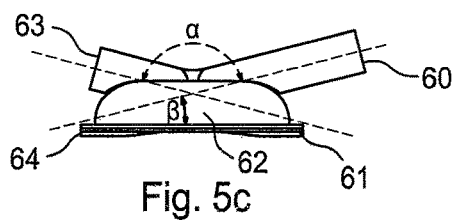
FIGS. 5a to 5d show detailed view of the dome cassette and its locking arrangement on the pressure measuring sensors.
Figure 5A:
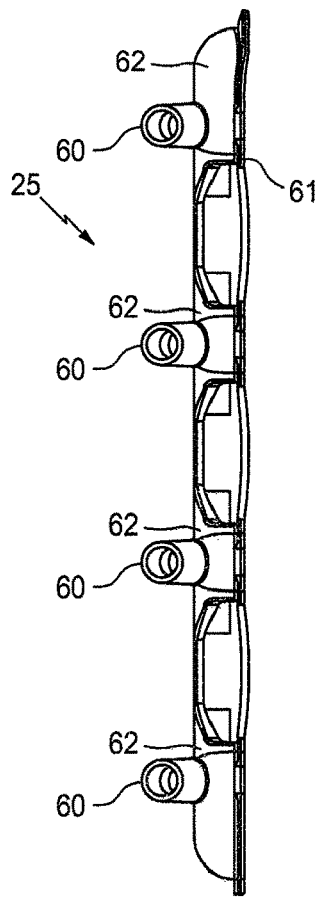
Figure 5B:
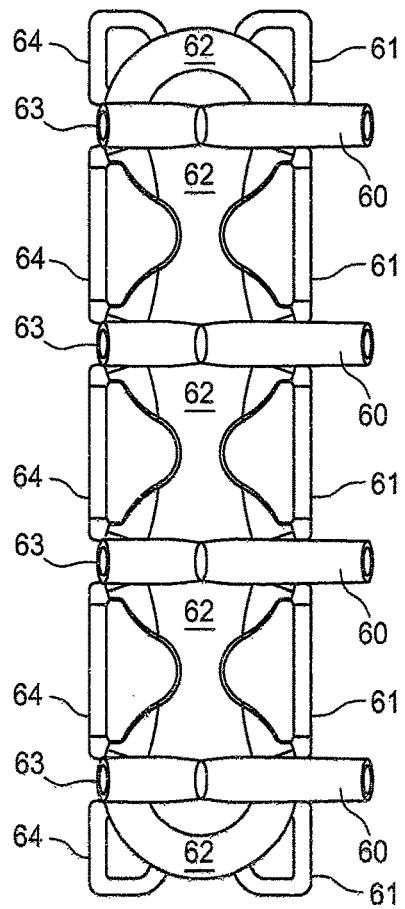

FIGS. 5a to 5d show detailed views of the dome cassette 25 and locking arrangement on the pressure measurement sensors. In FIG. 5a a side view of the dome cassette 25 is shown in which the connections 60, the pressing web 61 and parts of the fluid domes 62 can be seen. In FIG. 5b a view from above of the dome cassette 25 is shown in which the other connections 63 and the rear pressing web 64 can also be seen. FIG. 5c is a further side view in which in addition to the two connections 60 and 63 the two pressing webs 61 and 64 and the angle arrangement of the supply lines 60 and 63 with regard to each other with angle α and with regard to the base with angle β are shown.

Figure 5D:
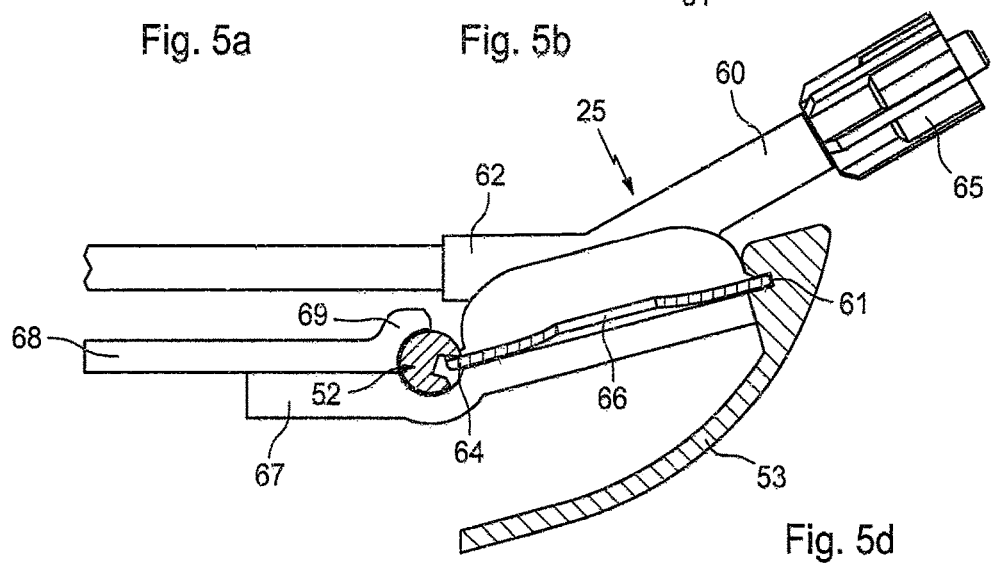

FIG. 5d shows the arrangement of the dome cassette 25 on the pressure measurement indicators, wherein the dome cassette 25 is aligned via the pressing web 61 in the holder 53 and fixed by means of the pressing roller 52 and its axial slit in combination with turning. The holder 53 also comprises the guide 69 and 68 as a direct or indirect component part of the holder, which in the corresponding positions also comprises the pressure measurement indicator (not shown here). In addition to the holder, in this view the connections 60 and 63 can also be seen, wherein the connection 60 also has a Luer lock 65.

Figure 6:
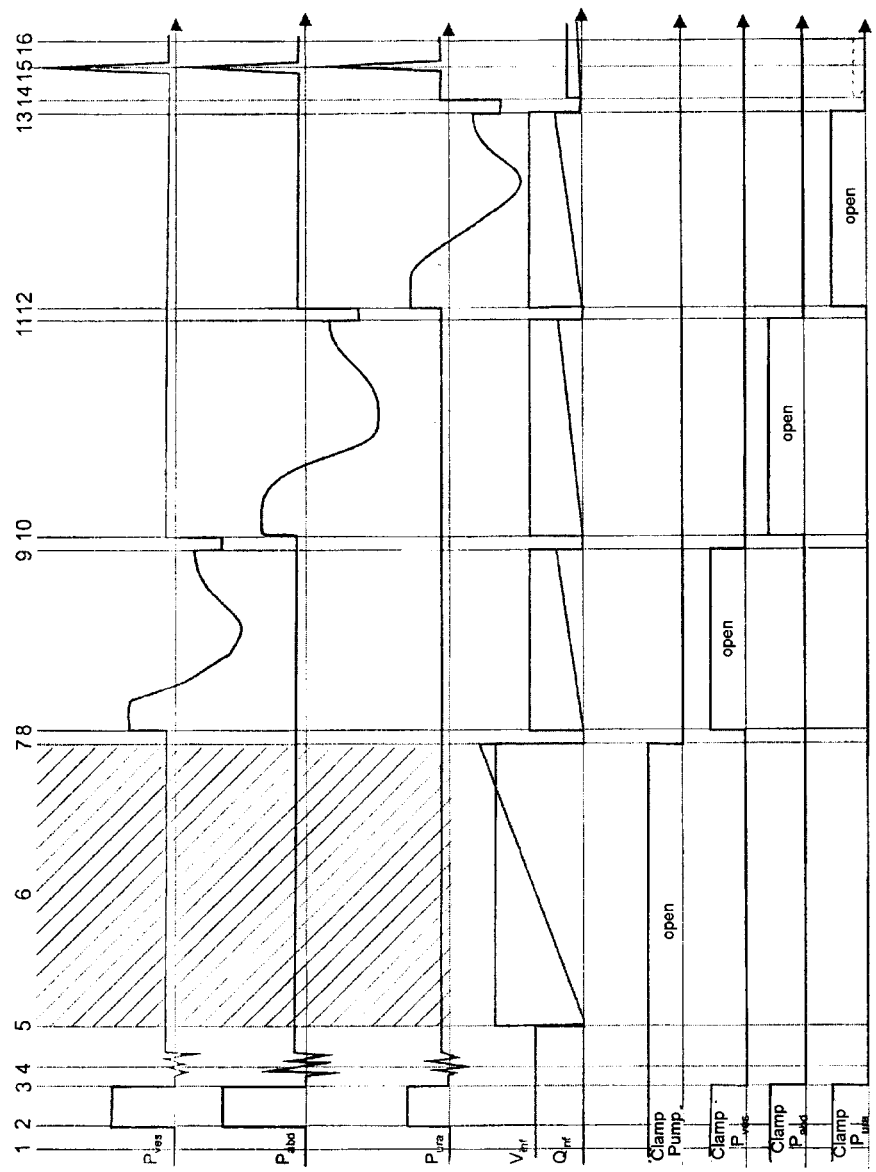
FIG. 6 shows a measuring protocol of automatic venting and zeroing of the pressure measuring system in accordance with the invention.

In FIG. 6 by way of the process stages the course of the pressure at the corresponding positions or settings of the components is shown. $P_{ura}$, $P_{ves}$, and $P_{abd}$ stand for the pressure in the corresponding pressure domes, $V_{inf}$ and $Qi_{nf}$ for the infusion volume and the fluid flow and clamp pump, clamp $P_{ura}$ and clamp $P_{abd}$ and clamp $P_{ves}$ for the switching position of the $P_{ura}$ clamp $P_{abd}$ corresponding tube clamp. The process is described as an example below:

1) The user places the dome cassette 25 of the pump tube 21 into the device and inserts the spike connection 30 into the infusion bag 20.
2) The locking mechanism is closed, whereby through the pressing pressure of the domes 25 on the sensors a pressure offset occurs.
3) The pressure offset is automatically balanced out (zeroed) after a material relaxation time of 5-10 seconds. At the same times the tube clamps 24 of the pressure channels 26 and 27 are closed.
4) The user places the transurethral catheter 29 in the bladder and the rectal catheter 28 in the rectum of the patient (if this has not already been done) and connects the pump tube 21 and the pressure transmission tubes with the Luer locks of the dome cassette 25. As of this moment the user can check the correct placement of the catheter 28, 29 by means of rest pressure values shown on the device, which are now measured via the air columns of the pressure transmission tubes and catheter lumen.
5) If the rest pressures show plausible values, the user starts the fully automatic venting and zeroing procedure by pressing a button on the device, whereupon the entire infusion line is vented.
6) In the hatched time interval all the measuring changes measure the rest pressure at the relevant measuring site via the air column. In order to minimise any fluctuations through movement of the patients or disturbances the average value measured by the channel during this period is calculated and subsequently use as the rest pressure value for zeroing.
7) As the volume of the infusion line (tube plus filling volume of the catheter) is precisely known and the quantity of the filling medium conveyed through the volume transducer and rotations of the rolling wheel of the pump 22 is constantly measured, the venting can be fully automatically ended when the water column reaches the filling lumen output. The pump tube clamp 24 is closed.
8, 10, 12) The venting of the pressure transmission tubes than always takes sequentially in the same way. The relevant tube clamp is opened, while all the others are closed and the pump conveys that filling medium at a defined filling rate through the relevant pressure transmission line. It should be noted, that during filling, due to the increasing water column a hydrostatic and also a dynamic component are increasingly added and no longer is the actual pressure at the measuring location determined.
9, 11, 13) As the volumes of the pressure transmission lines are known and the filling quantity is constantly measured the venting process can be fully automatically ended when the water column has reached the measuring lumen outputs. The pump 22 is stopped and the relevant tube clamp 24 closed. At this moment the device measures the current pressure at the measuring location in the body plus a hydrostatic pressure resulting from the unknown difference in height between the measuring location and the sensor. This is now fully automatically calculated by setting the measuring channel to the rest pressure measured via the air column in (6) by means of the software.
14, 15) The correct placement of the catheter is checked in a final stage by asking the patient to cough and comparing the resulting pressures peaks. For this the tube clamps 24 of all channels which required perfusion for the measurement ($P_{ura}$ in urodynamics) are automatically set to the perfusion setting and the pump 22 to perfusion speed.
16) The preparatory phase is completed and the actual measurement can begin.

The invention claimed is:

1. A device for measuring pressure in a fluid, comprising:
   a holder having a first clamping portion, a second clamping portion, and at least two pressure transducers arranged between the first and second clamping portions;
   each pressure transducer having a measurement surface;
   a cassette having at least two measurement chambers which can be filled with a fluid, wherein each measurement chamber is mechanically coupled to the measurement surface of a respective one of the pressure transducer by a membrane and each measurement chamber has at least two connection points for a fluid flow; and
   a pressing roller with which the cassette is fixed to the holder;
   wherein the cassette has two outer flanges positioned opposite each other, wherein one of the flanges engages in a clamping edge of the first clamping portion of the holder and the other flange engages in the pressing roller, wherein the pressing roller is held in a rotatable manner at the second clamping portion of the holder.

2. The device according to claim 1, wherein the connection points are arranged at an angle ($\alpha$) with regard to each other of 180° to 60°.

3. The device according to claim 1, wherein the connection points are arranged at an angle ($\beta$) of 0° to 60° with regard to the base area of the measurement chamber.

4. The device according to claim 1, wherein at least one of the connection points has a positive Luer lock connection or a negative Luer lock connection.

5. The device according to claim 1, wherein the interior of each measurement chamber has an essentially circular base area.

6. The device according to claim 5, wherein at least one of (i) the base area is open (ii) the membrane covers the open base area and (iii) the membrane is made of a material selected from a group which contains silicone, latex, rubber, and combinations thereof.

7. The device according to claim 1, wherein each membrane is an integral part of the respective measurement chamber.

8. The device according to claim 1, wherein each pressure transducer is an electromechanical pressure transducer and preferably at least the measuring area of the pressure transducer is covered by the respective membrane in a form-fitted manner and/or the measuring range of the pressure transducer is arranged centrically in relation to the base area of the respective measurement chamber.

9. The device according to claim 1, wherein through turning the pressing roller each measurement chamber, each membrane and the respective pressure transducer are connected to each other in a fluid-tight manner.

10. The device according to claim 1, wherein the interior of each measurement chamber is essentially dome-shaped and/or the dome-shaped interior is flattened in the central area.

11. The device according to claim 1, wherein each measurement chamber has a volume of between 0.1 cm$^3$ and 10 cm$^3$ and/or a base area of between 0.1 cm$^2$ and 5 cm$^2$.

12. The device according to claim 1, wherein the holder and/or the cassette are at least in sections of partially made of a material selected from a group that includes duroplastic or thermoplastic synthetic materials.

13. The device according to claim 1, wherein the pressing roller is capable of being moved by a motor.

14. The device according to claim 1 wherein the pressing roller can be force-fitted with the second clamping portion to be held in the rotatable manner.

* * * * *